(12) United States Patent
Schwartz

(10) Patent No.: US 6,776,984 B1
(45) Date of Patent: Aug. 17, 2004

(54) INDUCED REGENERATION AND REPAIR OF DAMAGED NEURONS AND NERVE AXON MYELIN

(76) Inventor: George R. Schwartz, P.O. Box 1968, Santa Fe, NM (US) 87504

( * ) Notice: Subject to any disclaimer, the term of this patent is extended or adjusted under 35 U.S.C. 154(b) by 0 days.

(21) Appl. No.: 09/642,236

(22) Filed: Aug. 17, 2000

Related U.S. Application Data

(63) Continuation-in-part of application No. 09/587,552, filed on Jun. 5, 2000, now abandoned, which is a continuation-in-part of application No. 09/499,198, filed on Feb. 7, 2000, now abandoned.
(60) Provisional application No. 60/150,040, filed on Aug. 20, 1999.

(51) Int. Cl.$^7$ .......................... A61K 38/00; A61K 45/00
(52) U.S. Cl. .................. 424/85.1; 424/198.1; 435/69.5; 530/351; 930/140; 514/18
(58) Field of Search .............................. 424/85.1, 198.1; 435/69.5; 530/351; 930/140; 514/18

(56) References Cited

U.S. PATENT DOCUMENTS

| | | | |
|---|---|---|---|
| 5,795,569 A | 8/1998 | Bartley et al. | 424/85.1 |
| 5,879,673 A | 3/1999 | Thomas | 424/85.1 |
| 5,980,885 A | 11/1999 | Weiss et al. | 424/93.21 |
| 5,989,537 A | 11/1999 | Holly et al. | 424/85.1 |

OTHER PUBLICATIONS

H. Heuer et al. "Expression of thyrotropin–releasing hormone receptor 2 (TRH–R2) in the central nervous system of rats." J. Comp. Heurol Dec. 11, 2000; 428(2): 319–36. Abstract.
Dept. of Physiology, Univ. of Mich. Med. Sch. "Thyroid hormone in neural rescue." Thyroid Feb. 1997; 7(1): 115–24. Abstract.
K. Nakanishi et al. "Thrombopoietin expression in normal and hypobaric hypoxia–induced thrombocytopenic rats." Laboratory Investigation, Jun., 1999; 79(6): 679–88. Abstract.
McMorris et al. "Regulation of Oligodendrocyte Development and CNS Myelination by Growth Factors: Prospects for Therapy of Demyelinating Disease." Brain Pathology 6: 313–329 (1996).
Rogister et al. "Oligodendrocytes: From Development to Demyelinated Lesion Repair." Acta. Neurol. Belg. 99: 32–39, (1999).
Franklin et al. "Remyelination in the CNS of the hypothroid rat." NeuroReport 7: 1526–1530 (1996).
Hinks et al. "Distinctive Patterns of PDGF–A, FGF–2, IGF–1 and TGF–β1 Gene Expression during Remyelination of Experimentally–Induced Spinal Cord Demyelination." Molecular and Cellular Neuroscience 14: 153–168 (1999).
Calver et al. "Oligodendrocyte Population Dynamics and the Role of PDGF in Vivo." Neuron 20: 869–882 (1998).
Rodriguez–Peña. "Oligodendrocyte Development and Thyroid Hormone." J. (1999). Neurobiol. 40: 497–512.

Li et al. "Thrombopoietin and its Alternatively Spliced Form are Expressed in Human Amygdala and Hippocampus." Blood 87(12): 5382–4 (1996).
Souyri. "Mp1: From an Acute Myeloproliferative Virus to the Isolation of the Long Sought Thrombopoietin." Seminars in Hematoloty 35(3): 222–231 (1998).
Dubois–Dalcq et al. "Why are growth factors important in oligodendrocyte physiology?" Pathologic Biologie 48: 80–86 (2000).
Grinspan et al. "Protein Growth Factors as Potential Therapies for Central Nervous System Demyelinative Disorders." Annals of Neurology 36: 5140–5142 (Supplement), (1994).
Vadhan–Raj. "Recombinant Human Thrombopoietin: Clinical Experience and In Vivo Biology," Seminars in Hematology 35(3): 261–268 (1998).
Barres et al. "Cell Death and Control of Cell Survival in the Oligodendrocyte Lineage." Cell 70: 31–46 (1992).
McMorris et al. "Regulation of Oligodendrocyte Development and Central Nervous System Myelination by Insulin–like Growth Factors." Ann. NY. Acad. Sci. 692: 321–34 (1993).
Herndon. "The Effect of Drugs on Oligodendrocyte Proliferation and Myelin Regeneration." Progress in Brain Research 71: 485–491 (1987).
Somlo et al. "Recombinant Human Thrombopoietin in Combination with Granulocyte Colony–Stimulating Factor Enhances Mobilization of Peripheral Blood Progenitor Cells, Increases Peripheral Blood Platelet Concentration, and Accelerates Hemotopoietic Recovery Following High–Dose Chemotherapy." Blood 93(9): 2788–2806 (1999).
Cohen et al. "Cyclic AMP Regulates PDGF–Stimulated Signal Transduction and Differentiation of an Immortalized Optic–Nerve–Derived Cell Line." The Journal of Experimental Biology 202: 461–473 (1999).
Fruttiger et al. "Defective Oligodendrocyte Development and Sever Hypomyelination in PDGF–A Knockout Mice." Development 126: 457–467 (1999).
Fressinaud et al. "Platelet–Derived Growth Factor Partly Prevents Chemically Induced Oligodendrocyte Death and Improves Myelin–Like Membrances Repair In Vitro." GLIA 16: 40–50 (1996).
Matsas et al. "The Functional Roles of Glial Cells in Health and Disease: Dialogue Between Glia and Neurons," *Advances in Experimental Medicine and Biology* Chapter 15. (1999).
Metcalf et al. "Thyrotropin–Releasing Hormone." Ann. NY Acad. Sci. 553: 422–430 (1989).

*Primary Examiner*—Christopher S. F. Low
*Assistant Examiner*—Chin-Min Kam
(74) *Attorney, Agent, or Firm*—Stephen A. Slusher; Peacock Myers & Adams, P.C.

(57) ABSTRACT

A method of treatment of and composition for human degenerative neurologic diseases discloses the administration of therapeutically amounts of an enhancement agent, such as thrombopoietin, to enhance the repair of neurons, including re-myelinization. A regulatory agent, such as thyroid hormone or thyrotropin, may also be included as part of the method and composition as a regulator of cell division and oligodendroglia production.

11 Claims, No Drawings

INDUCED REGENERATION AND REPAIR OF DAMAGED NEURONS AND NERVE AXON MYELIN

BACKGROUND OF THE INVENTION

This application is a continuation-in-part application of U.S. patent application Ser. No. 09/587,552 entitled "Method of Enhancement of Neurologic Recovery in Human Nervous System Damage by Use of Pharmaceutical Thrombopoietin", to George R. Schwartz, filed on Jun. 5, 2000, now abandoned, which in turn is a continuation-in-part of U.S. patent application Ser. No. 09/499,198, entitled "Method of Enhancement of Neurologic Recovery in Human Nervous System Damage by Use of Pharmaceutical Thrombopoietn," to George R. Schwartz, filed Feb. 7, 2000, now abandoned, and which claimed the benefit of U.S. Provisional Application Ser. No. 60/1 50,040, entitled "Method of Enhancement of Neurologic Recovery in Human Nervous System Damage by Use of Pharmaceutical Thrombopoietin", to George R. Schwartz, filed Aug. 20, 1999. The specification of each of the foregoing is incorporated herein by reference.

FIELD OF THE INVENTION TECHNICAL FIELD

This invention relates to treatment of human neurologic damage, and in particular to a method for increased regeneration and repair of damaged neurons and nerve axon myelin coatings, and nerve cell repair.

DESCRIPTION OF THE PREFERRED EMBODIMENTS

Best Modes for Carrying Out the Invention

Demyelination occurs when the myelin coating around nerve axons degenerates resulting in a defect in the ability to transmit nerve impulses. For example, multiple sclerosis is a disease of unknown cause in which degeneration occurs in the myelin sheath surrounding the nerves. This demyelination is also found in many other diseases such as transverse myelitis. Demyelination also occurs after trauma to the brain or spinal cord, after a stroke, in neurodegenerative diseases such as amyotropic lateral sclerosis and Alzheimer's disease, as well as in viral diseases including AIDS.

A cell type in the nervous system called the oligodendroglia is intimately involved in myelin regeneration, repair and maintenance of the nerve cells. Repair occurs by the repetitive wrapping of the plasma membranes of the oligodendroglia cells around damaged nerve cells and offers continuing metabolic nerve cell support. In the art, it has been established that for 0–2A progenitor cells that produce oligodendroglia cells proliferation is induced in culture by type-1 astrocytes. A recognized mitogen for 0–2A progenitor cells is platelet-derived growth factor (PDGF), and PDGF is a potent mitogen for 0–2A progenitor cells in vitro. Thus, laboratory experimentation has suggested that PDGF is crucial for the control of nerve cell repair and myelination in the nervous system.

It is also known in the art that the development of oligodendrocytes from precursor cells also includes an effector component which depends on thyroid hormone that stops cell division and initiates differentiation at the appropriate time.

Further, it is also known in the art that proteins generally referred to as thrombopoietins support biological activity that ultimately results in the production of platelets and other cells from the myeloid line, including markedly increasing PDGF production. Methods of preparation of thrombopoietin are disclosed in recent patents, for example, U.S. Pat. No. 5,795,569 issued to Amgen, Inc. and processes for producing them by recombinant genetic engineering techniques are also disclosed. Hence, the availability of thrombopoietins in pharmaceutically available quantities is to be expected in the near future.

SUMMARY OF THE INVENTION

A method of treatment of degenerative neurologic diseases provides for the administration of therapeutically effective amounts of an enhancement agent, such as thrombopoietin, to enhance the regeneration of neuron cells. A regulatory agent, such as thyroid hormone or thyrotropin, may also be included as a regulator of cell division and differentiation. The method may be used with humans and also with other mammals with neurologic damage.

The thrombopoietin may be orally ingested by the patient, or may be administered by intravenous, intramuscular or intrathecal injection.

The method can further include the step of administering thyroid hormone to the patient. The thyroid hormone may be orally ingested by the patient, or may be administered by intravenous, intramuscular or intrathecal injection. The thyroid hormone may include thyroid hormone extract or synthetic thyroid hormone.

The method can also further include the step of stimulating human thyroid production by administering thyrotropin to the patient. The thyrotropin may be orally ingested by the patient, or may be administered by intravenous, intramuscular or intrathecal injection.

The thrombopoietin may be isolated from a mammal, made by recombinant means, or made by synthetic means. It may be human thrombopoietin, a fragment of human thrombopoietin, or a variant polypeptide of human thrombopoietin. The therapeutically effective amount of thrombopoietin ranges from about 1.0 to about 100 $\mu$g/kg body weight per day.

In the method of this invention, the thyroid hormone can be co-administered to the patient with the thrombopoietin. In an alternative method, the thyrotropin can be co-administered to the patient with the thrombopoietin.

The invention further consists of a pharmaceutical composition for treatment of neurologic damage in a mammal, comprising thrombopoietin and thyroid hormone. The composition can contain between about 0.07 to about 10 mg of thrombopoietin per dose unit. The composition may be formulated such that it contains between about one and about three times as much thyroid hormone as thrombopoietin. In this composition, the thrombopoietin may be isolated from a mammal, made by recombinant means, or made by synthetic means. The thrombopoietin may be human thrombopoietin, a fragment of human thrombopoietin, or a variant polypeptide of human thrombopoietin. The thyroid hormone may be thyroid hormone extract or synthetic thyroid hormone.

The invention further consists of a pharmaceutical composition for treatment of neurologic damage in a mammal, comprising thrombopoietin and thyrotropin. The composition can contain between about 0.07 to about 800 mg of thrombopoietin per dose unit. In this composition, the thrombopoietin may be isolated from a mammal, made by recombinant means, or made by synthetic means. The thrombopoietin may be human thrombopoietin, a fragment of human thrombopoietin, or a variant polypeptide of human thrombopoietin.

A primary object of the present invention is to provide a method and formulation for neuron or myelin regeneration and maintenance in the nervous system.

Another object of the present invention is to provide a method for neuron and myelin regeneration and maintenance using endogenous platelet-derived growth factor (PDGF), production of which is induced by use of an enhancement agent.

Another object of the present invention is to increase PDGF production by administration of a therapeutically effective amount of thrombopoietin (TPO).

Another object of the invention is to provide a regulatory agent which effects a decrease in the rate of cellular division of oligodendrocytes and initiates differentiation into functional neuronal support cells.

Another object of the invention is to provide a method for treatment of neurological disorders including administration of TPO and co-administration or sequential administration of a regulatory agent, such as thyroid hormone, thyrotropin or the like.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS

Best Modes for Carrying Out the Invention

The present invention discloses a method of treatment of peripheral and central neurological diseases by the administration to patients of an enhancement agent in appropriate form and quantity. The treatment is disclosed for nervous system disorders, including diseases such as transverse myelitis, multiple sclerosis, demyelination occurring after trauma to the brain or spinal cord, as well as stroke, degenerative diseases such as Alzheimer's and amyotrophic lateral sclerosis, and viral diseases such as AIDS, as well as peripheral nerve injury. The enhancement agent serves to stimulate the production of oligodendroglia and other glial cells in the repair of damaged neurons and nerve axons incident to such diseases.

The enhancement agent may be thrombopoietin which may be administered as a liquid or solid in the form of oral tablets, intravenous injection, intrathecal injection or intramuscular injection, depending upon the course of therapy followed.

In a second embodiment of the invention, a regulatory agent is used, which may be thyroid hormone in the form of thyroid extract, stimulation of human production by thryrotropin (thyroid-stimulating hormone), or synthetic thyroid hormone combined with the enhancement agent therapy to regulate cell division and oligodendroglia production.

Prior to describing the present invention in detail, the following definitions are given:

Enhancement agent: Includes any substance which, when administered to a mammal, results in the direct or indirect production of platelet-derived growth factor (PDGF). Examples of enhancement agents include thrombopoietin (TPO) and other mpl ligands, variants and derivatives thereof, and the like.

Thrombopoietin: Includes TPO produced by any means, including TPO isolated from a mammal, made by recombinant means and made by synthetic means. TPO may be human TPO, a fragment of human TPO, a variant polypeptide of TPO, a chimeric polypeptide of any of the foregoing and the like. The TPO may further be modified, and may be pegylated, glycosolated and the like. The TPO may further be present in a formulation including one or more carriers or excipients. Various forms and formulations of TPO are described in, among others, U.S. Pat. Nos. 5,795,569; 5,879,673; and 5,989,537.

Regulatory agent: Includes any substance which, when administered to a mammal, results in the direct or indirect alteration of cell division rates and induction of differentiation, specifically of oligodendrocyte cells. Regulatory agents include thyroid hormone, thyrotropin and the like. The effort of these regulatory agents are described generally in Rodriguez-Pena A: Oligodendrocyte development and thyroid hormone. *J. Neurobiol* 1999, Sep. 15;40 (4):497–512; Ahlgren S C, Wallace H, Bishop J, Neophytou C, Raff MC: Effects of thyroid hormone on embryonic oligodendrocyte precursor cell development in vivo and in vitro. *Mol Cell Neurosci* 1997;9(5/6);420–32; Gao F B, Apperly J, Raff M: Cell-intrinsic timers and thyroid hormone regulate the probability of cell-cycle withdrawal and differentiation of oligodendrocyte precursor cells. Dev Biol 1998 May 1;197(1):54–66; and Durand B. Raff M: A cell-intrinsic timer that operates during oligodendrocyte development. Bioessays 2000 Jan; 22(1):64–71. The thyroid hormone, thyrotropin or the like may be isolated from a mammal, made by synthetic means, made by recombinant means, or made by any means known in the art. The regulatory agent may further be present in a formulation including one or more carriers or excipients.

The methods and substances of this invention may be used in the treatment of any of a variety of conditions resulting in neurological damage, including peripheral and central nervous system (CNS) injury, disease or disorders. CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, schizophrenia). In recent years neurodegenerative disease has become an important concern due to the expanding elderly population which is at greatest risk for these disorders. These diseases include Alzheimer's disease, multiple sclerosis (MS), Huntington's disease, amyotrophic lateral sclerosis, and Parkinson's disease. CNS disorders also encompass CNS trauma, such as results from stroke, epilepsy, traumatic injury and the like. Further, many viral diseases, including AIDS, result in CNS disorders.

The enhancement agent may be formulated as set forth above, and administered by any art conventional means. In the case of TPO, a therapeutically effective amount is administered, resulting in PDGF expression. Relatively low dosages may be employed, from about 1.0 to about 100 $\mu$g/kg body weight of the patient, and preferably about 5 to about 10 $\mu$g/kg body weight The TPO can be administered through various routes including via the nose or lung, cutaneously, subcutaneously, intrathecally, and preferably intravenously. Depending upon the route of administration, the TPO is preferably administered in combination with an appropriate pharmaceutically acceptable carrier or excipient. When administered systemically, the therapeutic composition should be pyrogen-free and in a parenterally acceptable solution. These conditions are generally well known and accepted to those of skill in the appropriate art.

Briefly, dosage formulations of the materials of the present invention are prepared for storage or administration by mixing the compound having the desired degree of purity with physiologically acceptable carriers, excipients and/or stabilizers. Such materials may include buffers such as phosphate, citrate, acetate and other organic acid salts; antioxidants such as ascorbic acid; low molecular weight peptides such as polyarginine, proteins such as serum albumen, gelatin or immunoglobulins; hydrophilic polymers such as polyvinylpyrrolidinone; amino acids such as glycine, glutamic acid, aspartic acid or arginine; monosaccharides, disaccharides and other carbohydrates including cellulose or its derivatives, glucose, mannose or dextrins; chelating agents such as EDTA; sugar alcohol such as mannitol or sorbitol; counter-ions such as sodium and/or non-ionic surfactants such as Tween, Pluronics or polyethylineglycol. The TPO may be administered as the free acid or base form or as a pharmaceutically acceptable salt.

The TPO may be administered in sustained-release formulations, including polymeric substrates, hydrogels, liposomes and the like.

The regulatory agent may similarly be formulated as set forth above, and administered by any art conventional means. In the case of thyroid hormone, therapeutically effective amounts may be employed, resulting in a decrease in cellular division of oligodendrocytes and further differentiation into functional neuronal repair cells.

Any of a variety of thyroid hormones may be employed as a regulatory agent, including but not limited to purified thyroid, levothyroxine, liothyronine, and thyroglobulin. These are available in oral tablet formulations, and in the case of levothyroxine, additionally as an injectable parenteral. In usual oral dosage forms, from about 0.10 to 0.125 mg per day of levothyroxine is administered, for liothyronine sodium from about 25 to 50 $\mu$g per day is administered, for thyroglobulin from about 32 to 160 $\mu$g per day is administered, and for dessicated thyroid from about 15 to 120 mg per day is administered. Combinations of the foregoing may also be administered, such as liotrix, a combination of levothyroxine and liothyronine. Injectable levothyroxine, from about 50 to 200 $\mu$g per day, may be injected into a muscle or into a vein.

Thyrotropin, also called thyroid-stimulating hormone, may alternatively be employed to increase endogenous thyroid production. Thyrotropin is available as an injectable parenteral. Thyrotropin may be produced by any means known in the art, including as a recombinant form of human thyroid-stimulating hormone. Sufficient thyrotropin is administered to increase thyroid levels to that desired, with monitoring as required by any of a variety of available thyroid assays.

In one embodiment, a patient with a CNS disorder is administered from about 1 to 50 $\mu$g/kg body weight of TPO by intravenous injection, with such injections occurring every 2 days for a period of at least 8 days. At a suitable time, such as 10 days after the initial injection of TPO, administration of thyroid hormone is initiated. The thyroid hormone administration, for example a Synthroid® preparation (levothyroxine), is at a rate of about 2 to 4 $\mu$g/kg body weight per day, and is continued for a suitable period, such as 21 days.

Multiple courses of therapy may be undertaken, such that TPO and thyroid hormone administration are alternated. There may also be periods of time between courses of therapy in which periods may be fixed or may be related to the onset of symptoms of CNS disorder.

The enhancement agent and regulatory agent may be co-administered, as part of a single formulation. Thus, a treatment regimen may be employed in which both TPO and thyroid hormone are co-administered. Alternatively, TPO may be initially administered without thyroid hormone and after a suitable period administration of a formulation including TPO and thyroid hormone or thyrotropin is initiated.

The invention is further illustrated by the following non-limiting examples.

EXAMPLE 1

B6SJL-TgN(SOD1-G93A)1 Gur strain mice were obtained from. The Jackson Laboratory, Bar Harbor, Me. The transgene in these mice carries a high copy number of a mutant allele human SOD1 containing the Gly93 →Ala (G93A) substitution (often referred to as G1H). Mice progressively become paralyzed in one or more limbs, with paralysis due to loss of motor neurons from the spinal cord. The mice are generally described in Gurney M E, Pu H, Chiu A Y, Dal Canto M C, Polchow C Y, Alexander D D, Caliendo J, Hentati A, Kwon Y W, Deng H X, Chen W, Zhai P, Sufit R L, Siddique T: Motor neuron degeneration in mice that express a human Cu,Zn superoxide dismutase mutation. *Science* 264:1772–1775 (1994), and use of these mice as a model of familial amyotrophic lateral sclerosis is described in Chiu A Y, Zhai P, Dal Canto M C, Peters T M, Kwon Y W, Prattis S M, Gurney M E: Age-dependent penetrance of disease in a transgenic mouse model of familial amyotrophic lateral sclerosis. *Mol Cell Neurosci* 6:349–362 (1995).

At 105 days following birth, mouse A began manifesting objective symptoms of limb paralysis. A protocol as described in Table 1 was followed.

TABLE 1

| Days Following Birth | Administration |
|---|---|
| 107 | 0.5 cc i.p. of a solution containing 1 $\mu$g/cc of thrombopoietin |
| 110 | 0.5 cc i.p. of a solution containing 1 $\mu$g/cc of thrombopoietin |
| 113 | 0.5 cc i.p. of a solution containing 1 $\mu$g/cc of thrombopoietin |
| 117 | 0.5 cc i.p. of a solution containing 1 $\mu$g/cc of thrombopoietin and 0.25 cc i.p. of a solution containing 500 $\mu$g/cc of thyrotropin releasing hormone |
| 119 | 0.5 cc i.p. of a solution containing 1 $\mu$g/cc of thrombopoietin |
| 121 | Synthroid ®, 0.1 mg in 2 ounces of drinking water, ad libitum |

The thrombopoietin was obtained from Rand D. Systems, Inc. (Minneapolis, Minn.) as carrier-free recombinant thrombopoietin and the thryrotropin was obtained from Ferring Pharmaceuticals; both were administered by intraperitoneal (i.p.) injection. Synthroid®, a form of levothyroxine, was obtained from Flint Pharmaceuticals in 100 $\mu$g tablets.

At day 111, marked improvement was observed, with elimination of shaking and limpness and improved muscle tone. At day 113, shaking resumed with observed early weakness developing. By day 115 marked hind limb weakness was observed. By day 118, decreased weakness was observed, although paresis remained in the left hind quarters. On day 120, increased mobility was observed. On day 122, marked improvement in front limbs was observed. Recurrence and increasing front limb weakness was observed on day 124. The mouse died at day 126.

EXAMPLE 2

A litter mate of mouse A, referred to as mouse B, was administered a protocol as described in Table 2, with administration commencing prior to the onset of any objective symptoms.

TABLE 2

| Days Following Birth | Administration |
|---|---|
| 87 | 0.5 cc i.p. of a solution containing 1 μg/cc of thrombopoietin |
| 91 | 0.5 cc i.p. of a solution containing 1 μg/cc of thrombopoietin |
| 93 | 0.6 cc i.p. of a solution containing 1 μg/cc of thrombopoietin |
| 95 | 0.5 cc i.p. of a solution containing 1 μg/cc of thrombopoietin |
| 105 | Synthroid ®, 0.1 mg in 4 ounces of drinking water, ad libitum through remaining life |
| 126 | 0.5 cc i.p. of a solution containing 1 μg/cc of thrombopoietin |

With this protocol, no objective signs were observed until day 121, when slight posterior weakness was noted. This was 16 days following onset of objective signs of illness in the litter mate mouse A. At day 129, posterior limb paralysis was observed, with the fore limbs remaining functional but weakness observed in the left front. The mouse died on day 132.

EXAMPLE 3

A B6SJL-TgN(SOD1-G93A)1Gur strain mouse as described in Example 1 was obtained, referred to as mouse C. Mouse C was administered a protocol as described in Table 3, with administration commencing prior to the onset of any objective symptoms.

TABLE 3

| Days Following Birth | Administration |
|---|---|
| 80 | 0.5 cc i.p. of a solution containing 1 μg/cc of thrombopoietin |
| 84 | 0.5 cc i.p. of a solution containing 1 μg/cc of thrombopoietin |
| 86 | 0.6 cc i.p. of a solution containing 1 μg/cc of thrombopoietin |
| 88 | 0.5 cc i.p. of a solution containing 1 μg/cc of thrombopoietin |
| 92 | Synthroid ®, 0.1 mg in 4 ounces of drinking water, ad libitum through remaining life |

With this protocol, no objective signs of illness were observed through day 110, more than two standard deviations from the expected onset of sickness (91±14 days).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of inducing regeneration and repair of nerve axon myelin coatings in a mammal with demyelination comprising:
    systemically administering sufficient quantities of thrombopoietin to the mammal to induce endogenous production of platelet-derived growth factor in the mammal; and
    systemically administering sufficient quantities of a thyroid hormone to regulate cell division and oligodendroglia production,
    whereby regeneration and repair of nerve axon myelin coatings in a mammal with demyelination is induced.

2. The method of claim 1 wherein the step of systemically administering the thrombopoietin comprises a method selected from the group consisting of oral administration, intravenous injection, intramuscular injection and intrathecal injection.

3. The method of claim 1 wherein the step of administering the thyroid hormone comprises a method selected from the group consisting of oral administration, intravenous injection, intramuscular injection and intrathecal injection.

4. The method of claim 1 wherein the thyroid hormone is a thyroid hormone extract.

5. The method of claim 1 wherein the thyroid hormone is a synthetic thyroid hormone.

6. A method of inducing increased platelet production with secondary increased endogenous production of platelet-derived growth factor in a mammal, the platelet-derived growth factor serving as a therapeutic agent to stimulate regeneration or repair of nerve axon myelin coatings in a mammal with damaged neurons, the method comprising:
    systemically administering sufficient quantities of thrombopoietin to the mammal to increase platelet production; and
    systemically administering sufficient quantities of a thyroid hormone to regulate cell division.

7. The method of claim 6 wherein the step of systemically administering the thrombopoietin comprises a method selected from the group consisting of oral administration, intravenous injection, intramuscular injection and intrathecal injection.

8. The method of claim 6 wherein the step of administering the thyroid hormone comprises a method selected from the group consisting of oral administration, intravenous injection, intramuscular injection and intrathecal injection.

9. The method of claim 6 wherein the thyroid hormone is a thyroid hormone extract.

10. The method of claim 6 wherein the thyroid hormone is a synthetic thyroid hormone.

11. A method of inducing increased platelet production with secondary increased endogenous production of platelet-derived growth factor in a mammal, the platelet-derived growth factor serving as a therapeutic agent to stimulate regeneration or repair of nerve axon myelin coatings in a mammal with damaged neurons, comprising:
    systemically administering from 1.0 to 100 μg/kg body weight per day of thrombopoietin to the mammal to induce endogenous production of platelet-derived growth factor in the mammal; and
    systemically administering a thyroid regulatory agent to regulate cell division and oligodendroglia production, the thyroid regulatory agent selected from the group consisting of from about 0.10 to 0.125 mg per day of oral levothyroxine, from about 25 to 50 μg per day of oral liothyronine sodium, from about 32 to 160 μg per day of oral thyroglobulin, from about 15 to 120 mg per day of oral dessicated thyroid, and from about 50 to 200 μg per day of injected levothyroxine.

* * * * *